(12) United States Patent
Jamoussi et al.

(10) Patent No.: US 9,201,045 B2
(45) Date of Patent: Dec. 1, 2015

(54) INTERNAL AND EXTERNAL UNIVERSAL EMAT INSPECTION DEVICES AND RELATED METHODS

(71) Applicant: itRobotics, Inc., Stafford, TX (US)

(72) Inventors: Anouar Jamoussi, Sugar Land, TX (US); Zhiyong Wang, Missouri City, TX (US); Bruce Maxfield, Buford, WY (US)

(73) Assignee: ItRobotics, Inc., Stafford, TX (US)

( * ) Notice: Subject to any disclaimer, the term of this patent is extended or adjusted under 35 U.S.C. 154(b) by 350 days.

(21) Appl. No.: 13/952,341

(22) Filed: Jul. 26, 2013

(65) Prior Publication Data
US 2014/0028300 A1    Jan. 30, 2014

Related U.S. Application Data

(60) Provisional application No. 61/676,911, filed on Jul. 28, 2012.

(51) Int. Cl.
*G01N 27/72* (2006.01)
*G01N 27/82* (2006.01)
*G01N 29/22* (2006.01)
*G01N 29/24* (2006.01)

(52) U.S. Cl.
CPC .............. *G01N 27/82* (2013.01); *G01N 29/225* (2013.01); *G01N 29/2412* (2013.01); *G01N 2291/0422* (2013.01); *G01N 2291/0423* (2013.01); *G01N 2291/2636* (2013.01)

(58) Field of Classification Search
CPC ................... G01N 27/82–27/83; G01N 27/87; G01N 29/225; G01N 29/2412; E21B 47/0905–47/091
USPC ............................ 324/220–221; 73/623–644
See application file for complete search history.

(56) References Cited

U.S. PATENT DOCUMENTS

| | | | |
|---|---|---|---|
| 4,471,658 A * | 9/1984 | Morimoto | 73/643 |
| 5,285,689 A * | 2/1994 | Hapstack et al. | 73/623 |
| 6,076,407 A * | 6/2000 | Levesque et al. | 73/623 |
| 6,215,836 B1 * | 4/2001 | Walker et al. | 376/260 |
| 6,904,818 B2 | 6/2005 | Harthorn | |
| 7,104,125 B2 | 9/2006 | Harthorn | |

(Continued)

OTHER PUBLICATIONS

R. van Agthoven, Ultrasonic Inspection of Risers a New and Simple Approach, 7th ECNDT, NDT.net—Nov. 1998, vol. 3, No. 11, http://ndt.net/article/ecndt98/pipeline/282/282.htm.

*Primary Examiner* — Patrick Assouad
*Assistant Examiner* — Demetrius Pretlow
(74) *Attorney, Agent, or Firm* — Bracewell & Giuliani LLP

(57) ABSTRACT

Systems, devices, and methods of inspecting a body of a tubular, are provided. An exemplary electro-magnetic acoustic transducers (EMAT) tubular inspection system for inspecting a body of a tubular includes an EMAT in-line tubular inspection device. The device can include a spine having a longitudinal support body and radially projecting rails, and multiple telescoping sections each connected to the radially projecting rails. The telescoping sections can include a magnetic back panel, one or more wheels positioned to engage an inner surface of a body of a tubular during inspection, and signal propagating and receiving modules carried by the magnetic back panel. Each module can include a magnet and different types of EMAT inspection transducer coil arrangements connected to the magnet. The different types of EMAT inspection transducer coil arrangements provide for the generation of NBSH, SW, and SV waves.

24 Claims, 11 Drawing Sheets

(56) References Cited

U.S. PATENT DOCUMENTS

| | | |
|---|---|---|
| 7,107,863 B2 | 9/2006 | Harthorn |
| 7,234,347 B2 | 6/2007 | Harthorn |
| 7,552,631 B2 | 6/2009 | Harthorn |
| 8,002,501 B2 | 8/2011 | Dos Santos |
| 8,319,494 B2 | 11/2012 | Simek |
| 2010/0199767 A1* | 8/2010 | Ganin ............................. 73/623 |
| 2010/0327858 A1* | 12/2010 | Simek et al. .................. 324/220 |

\* cited by examiner

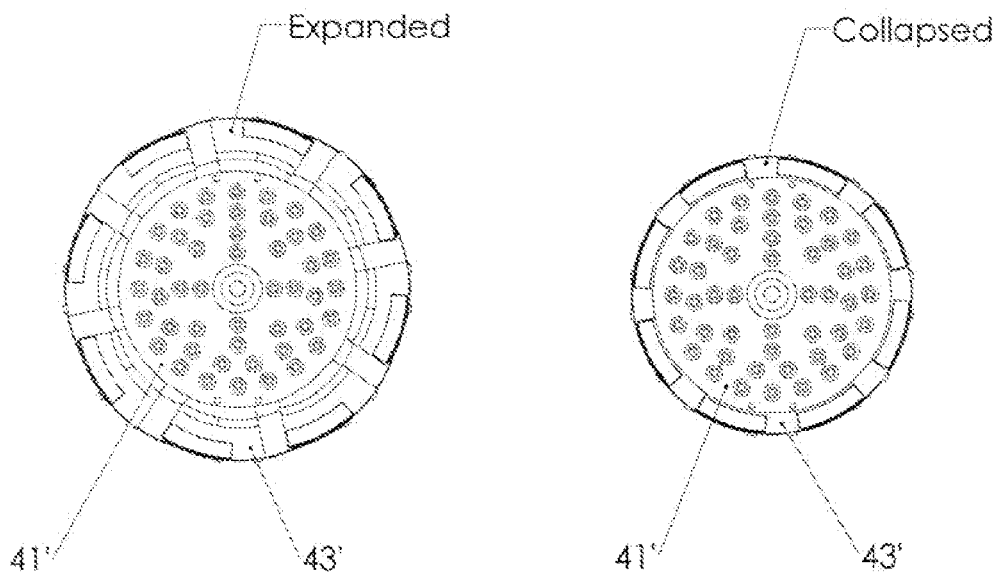
FIG. 13  FIG. 14
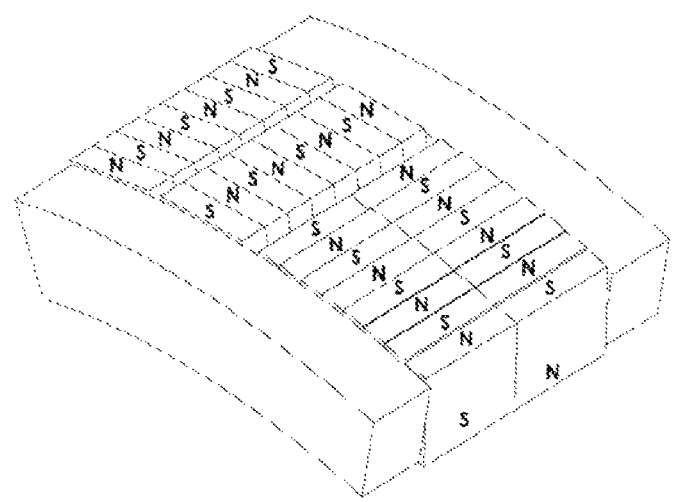
FIG. 15

INTERNAL AND EXTERNAL UNIVERSAL EMAT INSPECTION DEVICES AND RELATED METHODS

RELATED APPLICATIONS

This application is a non-provisional patent application of and claims priority to and the benefit of U.S. Patent Application No. 61/676,911, filed on Jul. 28, 2012, each incorporated by reference in its entirety.

BACKGROUND OF THE INVENTION

1. Field of the Invention

The present invention relates, in general, to the inspection of tubulars, and more specifically to systems, devices, and methods for inspecting a body of a tubular using an electromagnetic acoustic transducers.

2. Description of the Related Art

A drilling riser is a conduit that provides an extension of a subsea oil well to a surface drilling rig. Drilling risers are made up of pipe joints bolted together with flanges. Each joint is typically 18-24 inches in diameter and 70-100 feet in length, and can exceed one inch in wall thickness, which is considered a heavy wall. Normally, there are longitudinal and transverse welds in a joint. Over time of usage, a riser joint may develop wall thinning, corrosion, pitting, and cracks with various orientations on the interior and exterior surfaces. It may also contain mill defect such as delamination that, due to cyclic fatigue when in service, have grown beyond the maximum permissible size in new riser material.

Today, the offshore operators are strongly committed to protecting the environment. Pigging and riser inspection are performed periodically to determine the condition of the installation and the riser in particular. Such inspection plays a key role in ensuring the integrity, safety and security of the riser pipes.

For drilling riser joint type of pipes, the outer surface, however, is normally covered by a buoyancy jacket and possibly coated with an epoxy. Additionally, auxiliary lines, for example, for choke, kill, and hydraulic purposes, may be mounted off the center around the central riser pipe and being parallel to the pipe axis. Inspection from the outside requires removing the auxiliary lines, the buoyancy jacket and epoxy, and thus, is time consuming, cost prohibitive and impractical. Inspection from the inside, however, is more practical and can provide full coverage over the entire length of the riser joints.

There are several existing Non-destructive Testing (NDT) methods that can be employed in riser pipe inspection. Among them, conventional Ultrasonic Testing (UT) inspection method requires a couplant and a reasonably clean surface for good coupling of ultrasonic energy into the inspected material. The Magnetic Flux Leakage (MFL) inspection method needs to magnetize the inspected material to near magnetic saturation. Thus, it is not effective on heavy wall thicknesses. Moreover, the magnetic permeability within a typical weld seam varies drastically, making MFL impractical for weld inspection. The Eddy Current (EC) inspection method has limited depth of penetration, and thus, can only detect surface or near surface defects. Other NDE methods that are commonly used in the field, e.g. Magnetic Particle Testing (MT) and Penetrant Testing (PT), are slow due to the manual processes involved and require access to the surface being inspected. The remote field EC (RFEC) method is used for Outer Diameter (OD) and Inner Diameter (ID) defect detection and sizing. It has been used up to at least 15 mm wall and could possibly be used for thicker wall. Likely problems, however, are speed and sensitivity, but new signal processing methods should help in this area.

A riser pipe inspection job typically includes measuring the wall thickness and detecting on the ID or OD of the main body any longitudinal and transverse cracks, corrosion, and pitting. In addition, the inspection should be able to detect longitudinal and transverse weld imperfections, such as cracks, lack of fusion, and porosity, and subsurface defects such as delamination. This represents a situation where many types of defects need to be detected in one scan by one inspection tool. A thorough inspection in this situation requires a combination of multiple NDT techniques, such as UT, MFL, MT, and PT, and possibly multiple tools. Such combined inspections are usually economically prohibitive.

Electromagnetic acoustic transducer (EMAT) inspection techniques for non-contact ultrasound generation and reception have been used in some industrial applications. The inventors have recognized that EMAT has certain advantages over the above described industry-accepted techniques. For example, EMAT techniques can provide the benefits that the UT technique has to offer, e.g. the superior depth of penetration for flaw detection or measurement, but is better than UT due to the non-contact nature and no-couplant requirement capability. Also recognized is that the EMAT technique has less stringent requirements on surface cleaning and allows faster inspection speed.

Accordingly, recognized by the inventors is the need for systems, devices (tools), and methods for inspecting a body of the tubular such as a riser pipe, that can leverage advantages of EMAT with an innovative, with a tool/device containing multiple tightly packed high-performance EMAT configurations to detect the wide range of defects that may be encountered in a typical tubular inspection, and to provide 100% coverage of the inner diameter and outer diameter surfaces and the volume in between, over the entire length of the pipe being inspected even when the inner diameter of the pipe changes due to deformation of the pipe or buildup of particulate matter.

SUMMARY OF THE INVENTION

In view of the foregoing, various embodiments of the present invention advantageously provide systems, devices (tools), and methods of inspecting the body of a riser pipe or other tubular, which leverage advantages of EMAT, with an innovative tool/device containing multiple tightly packed high-performance EMAT configurations to provide 100% coverage of the inner diameter and outer diameter surfaces and the volume in between, over the entire length of the pipe being inspected even when the inner diameter of the pipe changes due to deformation of the pipe or buildup of particulate matter.

According to various embodiments of the systems and devices, the EMAT transducers are configured with different combinations of magnetic field direction and electrical coil forms to generate various wave modes, some of which are difficult to generate with conventional UT. These wave modes, generated by a single device/tool, can beneficially be used to achieve a wide range of measurement and detection capabilities to achieve reliable detection of a wide range of defect types that otherwise would have required a combination of different inspection methods using multiple different tools.

Most EMAT methods have at least a 20 db higher insertion loss than other forms of ultrasonic wave generation. Accordingly, various embodiments of the systems and devices advantageously provide higher power excitation, shielding from external electromagnetic noise and careful consideration of various aspects of the EMAT system instrumentation in the system and device designs. Compared to MFL, the various embodiments of the devices/tools can advantageously work with heavy wall thickness, can inspect welds, and can inspect pipes made of non-ferromagnetic conducting materials.

More specifically, an example of an embodiment of an EMAT tubular inspection system for inspecting a body of a tubular includes an EMAT in-line tubular inspection device or tool head and a set of external subsystems connected by an umbilical or self-propelled and wirelessly connected to the external subsystems. An embodiment of the tubular inspection device includes a spine having a longitudinal support body, a plurality radially projecting rails, and a plurality of telescoping sections each connected to at least two of the plurality of radially projecting rails. Each of the plurality of telescoping sections can include an e.g., magnetic, back panel, one or more guide mounts each including one or more surface engagement mechanisms (e.g. wheels) positioned to engage an inner surface of a body of a tubular during inspection thereof, and a plurality of signal propagating and receiving modules carried by the magnetic back panel. Each module can include a magnet operably connected to the magnetic back panel and a plurality of different types of EMAT inspection transducer coil arrangements operably connected to an outer surface portion of the magnet, the plurality of different types of EMAT inspection transducer coil arrangements providing for the generation of Normal Beam Shear Horizontal (NBSH), Surface Wave (SW), and Shear Vertical (SV) waves.

According to an embodiment, each module of the plurality of signal propagating and receiving modules can also or alternatively include transducer transmitting and receiving coils oriented substantially parallel with a longitudinal axis of the longitudinal support body of the spine of the in-line tubular inspection device. According to an embodiment, each module of the plurality of signal propagating and receiving modules can also include a second plurality of the different types of EMAT inspection transducer coil arrangements connected to a second outer surface portion of the magnet to provide for the generation of NBSH, SW, and SV waves, and respective transducer transmitting and receiving coils oriented substantially perpendicular to the longitudinal axis of the longitudinal support body of the spine.

According to an embodiment, a first plurality of different types of EMAT inspection transducer coil arrangements includes a first NBSH transmitter-receiver coil, a first surface wave-shear vertical transmitter coil, and a first plurality of surface wave-shear vertical receiver coils each oriented substantially parallel with the longitudinal axis of the spine of the in-line tubular inspection device, and a second plurality of different types of EMAT inspection transducer coil arrangements comprises a second NBSH transmitter-receiver coil, a second surface wave-shear vertical transmitter coil, and a second plurality of surface wave-shear vertical receiver coils each oriented substantially perpendicular with the longitudinal axis of the spine of the in-line tubular inspection device. According to this embodiment, the second NBSH transmitter-receiver coil is arranged to propagate shear horizontal wave signals polarized in a direction orthogonal to the polarization direction of corresponding shear horizontal wave signals by the first NBSH transmitter-receiver coil to thereby enhance defect detection in multiple directions. In this embodiment, both the shear horizontal waves propagated by the first NBSH transmitter-receiver coil and by the second NBSH transmitter-receiver coil propagate in a direction normal to the inner surface of the body of the tubular adjacent to the respective first and second NBSH transmitter-receiver coil. Also or alternatively, the second surface wave-shear vertical transmitter coil is arranged to propagate surface wave signals in a direction along the inner surface of the body of the tubular adjacent to the surface wave-shear vertical transmitter coil and orthogonal to the propagation direction of the surface wave signals generated by the first surface wave-shear vertical transmitter coil, and to propagate shear vertical wave signals in a direction orthogonal to the propagation direction of corresponding signals generated by the first surface wave-shear vertical transmitter coil to thereby enhance defect detection in multiple directions.

In order to enhance detection coverage, according to an embodiment of the invention, each of the plurality of telescoping sections also or alternatively includes a plurality of wedge-shaped subsections each having a radial cross-section described by a pair of converged lateral sides, a concave inner surface, and a convex outer surface and sharing the magnetic back panel for the respective telescoping section, with each of the plurality of wedge-shaped subsections containing a separate one of a plurality of guide mounts (e.g. wheel mounts).

Also or alternatively, according to an embodiment, the plurality of telescoping section are staggered in an overlapping manner to achieve full 100 percent coverage of ID and OD surfaces and volume therebetween over a entire length of the body of the tubular during inspection thereof. In this embodiment, the body of the tubular is characterized by having inner diameter that varies due to deformation in one or more portions of the body of the tubular or buildup of non-tubular material.

Also or alternatively, the plurality of telescoping section are staggered in an overlapping manner to ensure full 100 percent coverage over the inner surface of the body of the tubular during inspection thereof, with up to approximately ±10 percent of variation in inner diameter (ID) from the nominal size thereof. According to an exemplary configuration of this embodiment, the plurality of telescoping sections slidably engage at least two of the plurality of rails to expand due to an increase in inner diameter of the body of the tubular during inspection thereof and to thereafter retract due to a decrease in inner diameter. In this configuration, an overlap between extended ends of neighboring sections is sufficient so that a corresponding reduction in the overlap resulting from expansion resulting from the increase in inner diameter of the body does not generate a circumferential gap between the plurality of telescoping sections sufficient to reduce coverage below 100 percent when the variation in the inner diameter from the nominal size thereof is less than the approximately ±10 percent.

According to an embodiment, the plurality of different types of EMAT inspection transducer coil arrangements for each of multiple of the plurality of signal propagating and receiving modules for each of multiple of the plurality of telescoping sections also or alternatively include a surface wave-shear vertical transducer coil arrangement consolidating transmitting and receiving functions for an associated combination of surface and shear waves into a respective common transmitting coil using a different set of driving frequencies and excitation currents applied thereto to produce the respective surface wave and shear wave having vertical polarization. Further, each of the modules include a respective common set of one or more receiver coils, with each of the common transmitting and receiving coils positioned within a common magnetic field. The arrangement advantageously reduces total size of the inspection device.

According to an embodiment, the spine further carries an electronics assembly including electronics components configured to provide for detection of volumetric flaws, planar flaws along three reference orientations, and oblique flaws at non-zero angles from the three reference orientations, in the body of the tubular, the electronics components including a system controller, a received signal digitizer, and a received signal processing unit.

Various embodiments of the invention also include methods of inspecting a body of a tubular. An exemplary method can include the steps of positioning an in-line tubular inspection device to establish a magnetic field between each of a plurality of telescoping sections of the device and respective portions of the body of the tubular adjacent thereto and to form a magnetic coupling with the respective adjacent portion of the body of the tubular, and maintaining a preselected distance between a plurality of different types of EMAT inspection transducer coil arrangements of each of one or more signal propagating and receiving modules of each of the plurality of telescoping sections, and inner surface portions of the body of the tubular adjacent thereto through employment of a respective one or more guide mounts and through the maintaining of the magnetic coupling with the respective adjacent portion of the body of the tubular. The steps can also include sending electrical signals having a preselected duration, frequency, and sequence to a transmitter coil of each of the plurality of different types of EMAT inspection transducer coil arrangements to thereby generate NBSH, SW, and SV waves, receiving signals produced as a result of the step of sending the electrical signals, and conditioning and amplifying the received signals to thereby identify a plurality of flaws in the body of the tubular, the plurality of flaws comprising volumetric flaws, planar flaws along three reference orientations, and oblique flaws at non-zero angles from the three reference orientations.

According to an embodiment, each of the plurality of telescoping sections slidably engage at least two of a plurality of radially projecting rails to expand due to an increase in inner diameter of the body of the tubular during inspection thereof and to thereafter retract due to a decrease in inner diameter. In this embodiment, the step of maintaining a preselected distance also or alternatively includes automatically radially retracting one or more of the plurality of telescoping sections responsive to encountering an area of reduced inner diameter of the body of the tubular resulting from a deformation in the respective area of the body of the tubular or buildup of non-tubular material, and automatically radially extending the one or more of the plurality of telescoping sections responsive to passage of the area of increased inner diameter.

According to an embodiment, the plurality of telescoping sections are staggered in an overlapping manner to achieve full 100 percent coverage of ID and OD surfaces and volume therebetween over a entire length of the body of the tubular during inspection thereof within a substantial predetermined variation in ID from the nominal size thereof. In this embodiment, the body of the tubular is characterized by having inner diameter that varies due to deformation in one or more portions of the body of the tubular or buildup of non-tubular material. In this embodiment, this configuration can function such that the overlap between extended ends of neighboring sections is sufficient so that a corresponding reduction in the overlap resulting from expansion resulting from the increase in inner diameter of the body does not generate a circumferential gap between the plurality of telescoping sections sufficient to reduce coverage below 100 percent when the variation in the inner diameter from the nominal size thereof is less than approximately ±10 percent.

According to an embodiment, a magnetic field generator of each of the one or more signal propagating and receiving modules of one or more of the plurality of telescoping sections is a corresponding radially magnetized magnet. In this embodiment, the plurality of different types of EMAT inspection transducer coil arrangements include a first plurality of different types of EMAT inspection transducer coil arrangements operably connected to a first outer surface portion of the magnet, with the respective transmitting and receiving coils oriented substantially parallel with a longitudinal axis of a longitudinal support body of a spine of the in-line tubular inspection device. The coil arrangements also include a second plurality of the different types of EMAT inspection transducer coil arrangements connected to a second outer surface portion of the magnet, with the respective transducer transmitting and receiving coils oriented substantially perpendicular to the longitudinal axis of the longitudinal support body of the spine.

According to an embodiment, the transmitter coil and one or more receiver coils for one of the plurality of different types of EMAT inspection transducers for the one or more signal propagating and receiving modules for each of multiple of the plurality of telescoping sections are comprised by a surface wave-shear vertical transducer coil arrangement consolidating transmitting and receiving functions for an associated combination of surface and shear waves into a respective common transmitting coil using a different set of driving frequencies and excitation currents applied thereto to produce the respective surface wave and shear wave having vertical polarization, and a respective common set of one or more receiver coils. In this embodiment, each of the common transmitting and receiving coils are positioned within a common magnetic field produced by a magnetic field generator of the one or more signal propagating and receiving modules. The arrangement advantageously reduces total size of the inspection device.

Advantageously, various embodiments of the present invention provide three types of carefully configured EMAT transducers, namely the Normal Beam Shear Horizontal (NBSH) and Surface Wave (SW) and Shear Vertical (SV) EMATs, packaged into a single inspection tool in a staggered manner to achieve full (100%) coverage of the ID and OD surfaces and the volume in between over the entire length of the pipe even when the ID of the pipe changes slightly due to deformation or buildup. Advantageously, in order to further compact the tool, the SV waves drive and signal conditioning electronics can use the same transmitter and receiver arrangement, respectively, as used by the surface wave drive and signal conditioning to thereby provide an additional set of information with only the addition of wave mode specific signal processing. Additionally, a single signal processing unit can provide for SV, SW, and NBSH wave development for each module and for each of multiple modules. One or more of these features, but preferably all of them, enable high performance of the tool within a compact tool size.

Advantageously, according to various embodiments, to ensure 100 percent coverage and to further maximize redundancy, the NBSH EMATs can be arranged with two orthogonal polarization directions and the SW/SV EMATs can be arranged with two orthogonal propagation directions for the greatest probability of detection of defects in different directions, including but not limited to far and near wall corrosion, pitting, transverse and longitudinal cracks in pipe body, transverse and longitudinal weld defects, delamination, and wall thickness measurement. Advantageously, according to various embodiments the EMAT inspection tool measures wall thickness and detects all the above defects with one tool, in one scan, with 100% coverage and high spatial resolution, using a reasonable number of channels while keeping the cost relatively low.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 13 is a schematic diagram of a side view of the device of FIG. 11 having expanded telescoping sections according to an embodiment of the present invention.

FIG. 14 is a schematic diagram of a side view of the device of FIG. 11 having collapsed telescoping sections according to an embodiment of the present invention.

FIG. 15 is a perspective view of an alternating magnet block according to an embodiment of the present invention.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 1:
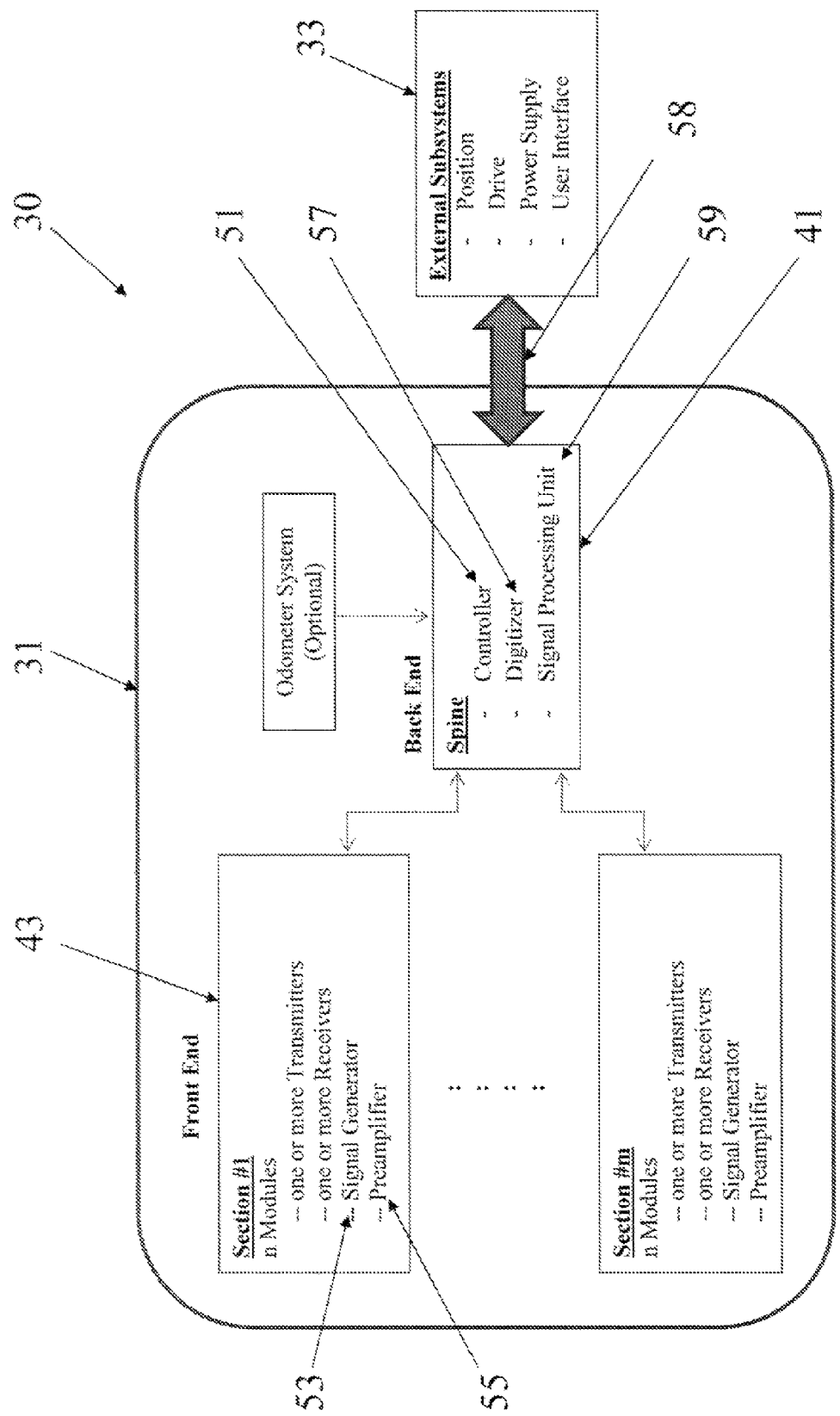
FIG. 1 is a schematic block diagram of a general system architecture of a system for inspecting a body of a tubular according to an embodiment of the present invention.

FIG. 1 illustrates an example of an embodiment of an EMAT tubular inspection system 30 for inspecting a body of a tubular such as, for example, a riser. According to the illustrated embodiment, the system 30 includes an EMAT in-line tubular inspection device or tool head 31 and a set of external subsystems 33 normally connected by an umbilical 35. In an alternative embodiment, the external subsystems 33 are connected wirelessly and the devices/tool head 31 includes a remote power source such as, for example, a high-capacity battery or capacitor (not shown).

Figure 2:
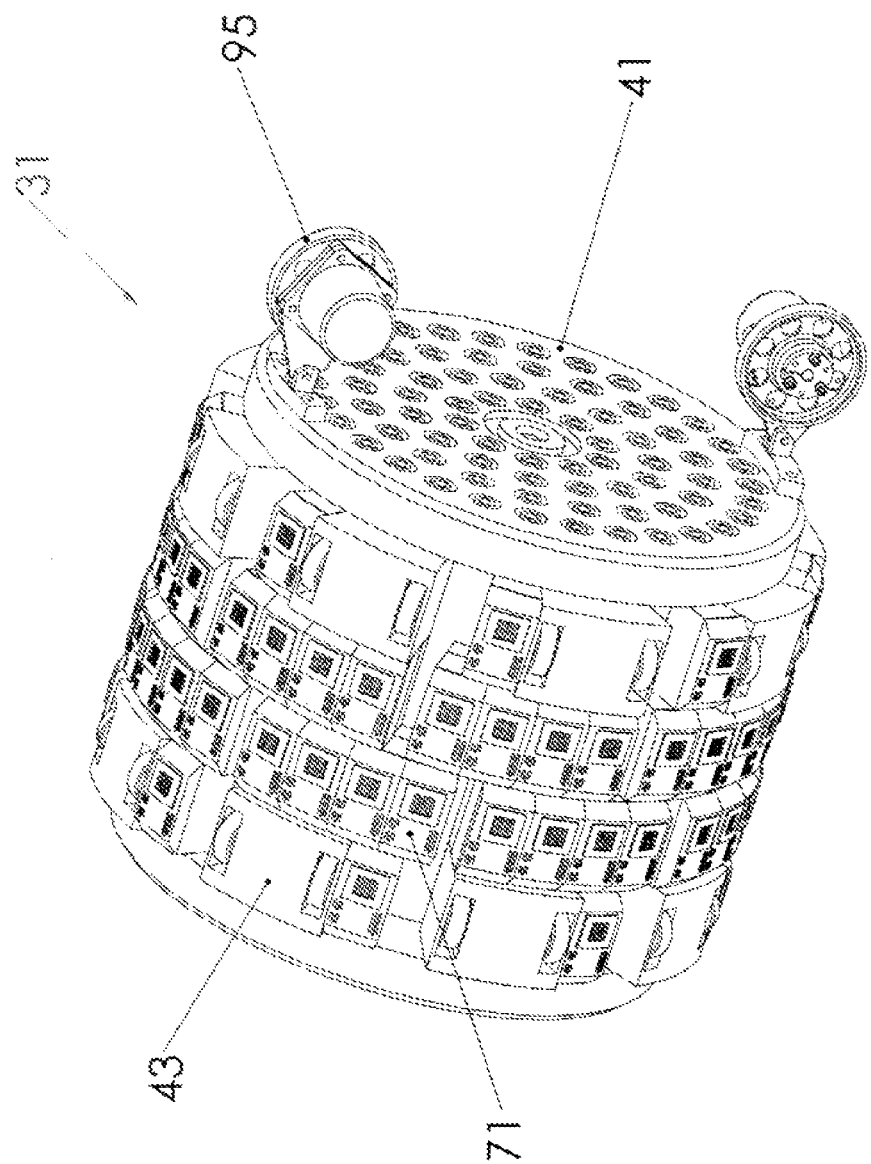
FIG. 2 is a perspective view of the side of an in-line tubular inspection device according to an embodiment of the present invention.
Figure 4:
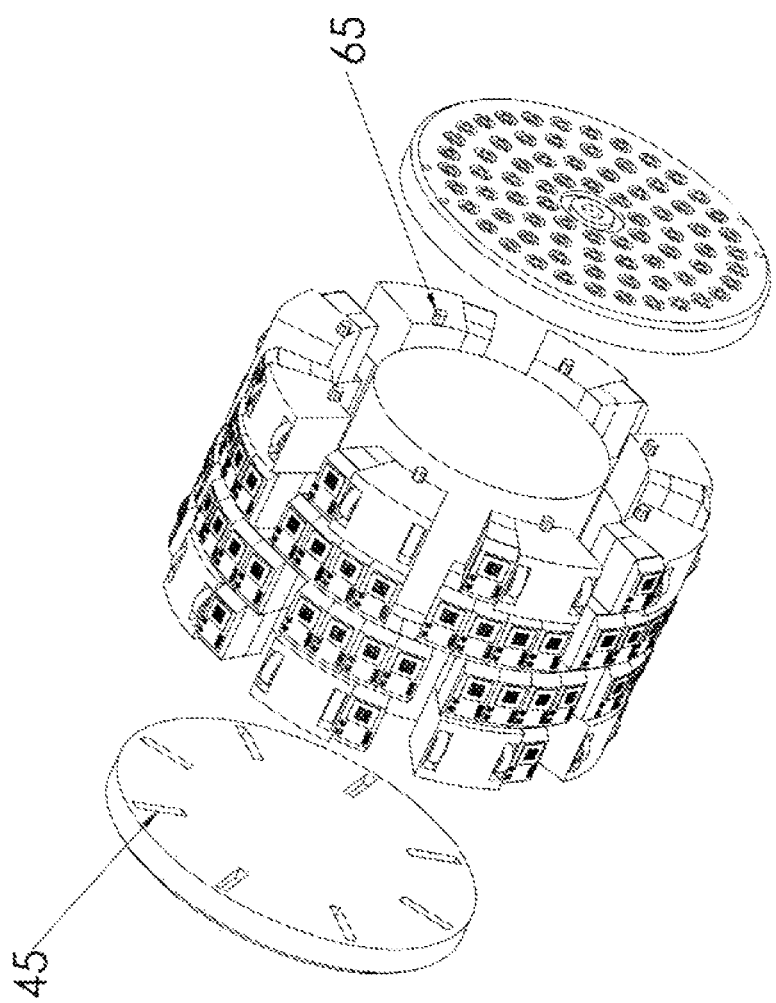
FIG. 4 is a perspective, partially exploded view of the side of an in-line tubular inspection device of FIG. 2 according to an embodiment of the present invention.
Figure 6:
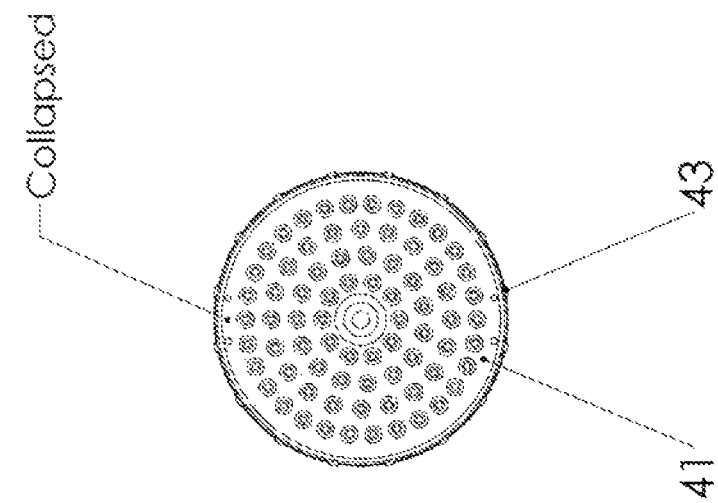
FIG. 6 is a schematic diagram of a side view of the device of FIG. 2 having collapsed telescoping sections according to an embodiment of the present invention.
Figure 5:
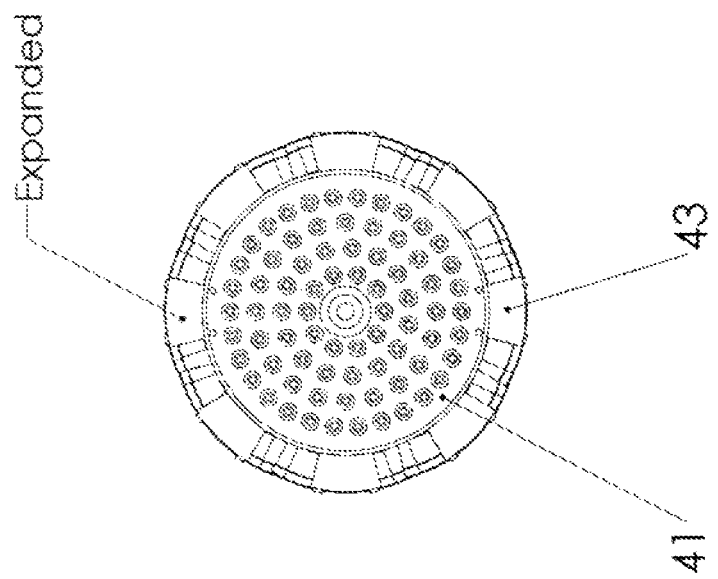
FIG. 5 is a schematic diagram of a side view of the device of FIG. 2 having expanded telescoping sections according to an embodiment of the present invention.

FIG. 2 illustrates an embodiment of the EMAT in-line or internal riser or other tubular inspection device/tool head 31. The tool head 31 includes a spine 41 located at the center of the tool 31 and a plurality of telescoping sections 43 mounted on the spine 41 and distributed along the circumference of the tool 31. The spine 41 includes a set of radially rails 45 (FIG. 4) along which the sections 43 can expand (FIG. 5) or collapse (FIG. 6). According to an exemplary configuration, the rails 45 are formed of a non-magnetic material as a part of the spine 41. The telescopic feature provides radial flexibility that provides the ability of the telescoping sections 43 to maintain contact with the inner surface of the pipe even when the pipe has irregular inner pipe diameters such as, for example, as a result of deformations or buildup of material inside the pipe which may affect only some of the telescoping sections, and to accommodate pipes having a larger inner diameter than the minimum outer diameter size of the tool 31.

As further shown in FIG. 1, the spine 41 also houses the back end electronics, including but not limited to the system controller 51 a received signal digitizer 57 (e.g., analog-to-digital converter), and the signal processing unit 59 in communication with the digitizer 57. According to the exemplary configuration, the system controller 51 coordinates the timing between the tone burst generation for transmitter coils (described below) and the sampling of the receiver signal digitizer 57. The digitizer 57 takes the analog output of the final amplification circuit 55 and converts it into digital signal. The digital signal is further processed by the signal processing unit 59, which according to the exemplary configuration, utilizes Field-Programmable Gate Arrays (FPGA) to allow the efficient execution of processing algorithm such as digital filtering and correlation processing, also known as matched filtering or pulse compression. The digital filtering and correlation processing capabilities of the backend electronics can serve to optimally enhance the low initial Signal-to-Noise Ratio (SNR) commonly encountered from the EMAT receiver coils to a surprising level.

Figure 3:
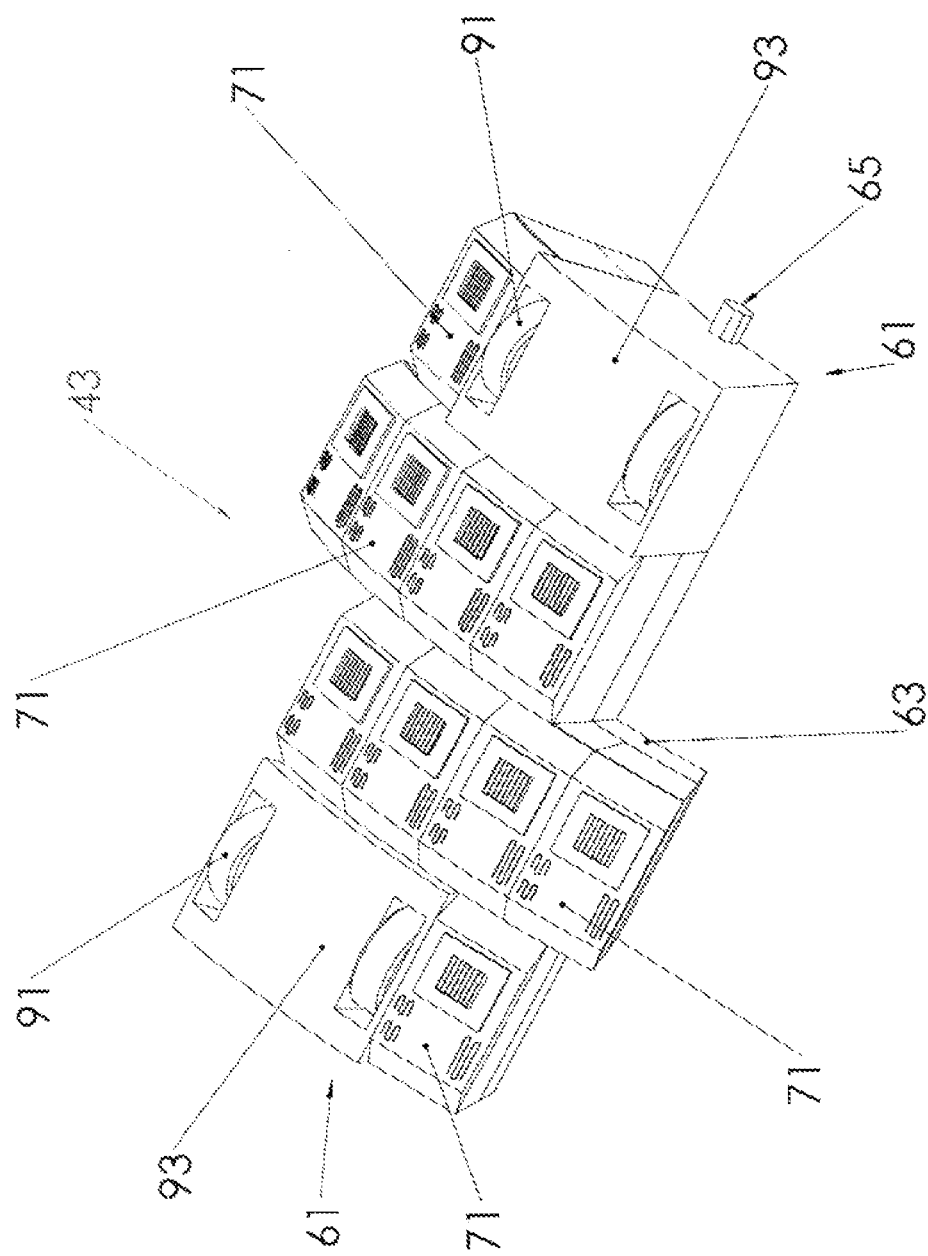
FIG. 3 is a perspective view of the top of a telescoping section of the in-line tubular inspection device of FIG. 2 according to an embodiment of the present invention.

As shown in FIG. 3, according to the exemplary configuration, each telescoping section 43 includes a plurality of wedge-shaped subsections 61, which have a radial cross-section described by a pair of converged lateral sides, a concave inner surface, and a convex outer surface. The subsection 61 each sharing a magnetic back panel (e.g. iron) 63 for the respective telescoping section. The telescoping sections 43/subsections 61 are mounted on the radially oriented rails 45 (FIG. 4) via an extension peg 65 so that the sections 43/subsections 61 together collectively form a flexible axially wedged cylinder capable of traversing pipe with an internal diameter greater or equal to the diameter of the cylinder created by the telescoping sections 43 in their fully collapsed configuration.

Figure 7:
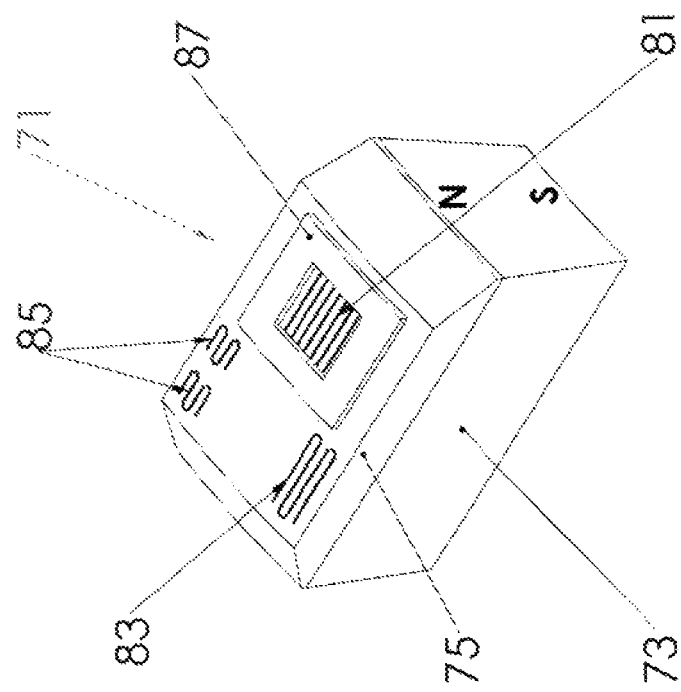
FIG. 7 is a perspective view of section module according to an embodiment of the present invention.

As shown in FIG. 7, each telescoping section 43 contains multiple functional modules 71. According to the exemplary configuration, each module 71 includes a magnet 73 magnetized in the radial direction and incorporating a pole cap 75 made out of ferromagnetic material for concentrating the magnetic field in the pipe wall. Note, alternative configurations can include those without pole caps and with magnetization parallel to the surface.

According to the exemplary configuration, each module 71, considered the building block of the tool 31, can also include the front end electronics and coils in axial and circumferential directions tightly packaged together. The front electronics can include, for example, a signal generator 53 in communication with the controller 51 (FIG. 1), a NBSH transmitter-receiver coil 81, a surface wave-shear vertical transmitter coil 83, and a plurality of surface wave-shear vertical receiver coils 85 each oriented substantially parallel with the longitudinal axis of the spine 41, and a pre-amplifier/amplifier 55 in communication with the digitizer 57. Note, as described in more detail later, the transmitter coil driving circuits can be co-located with the respective transmitter coils. Additionally, receiver coil preamplifiers can be co-located with their respective receiver coils.

Figure 8:
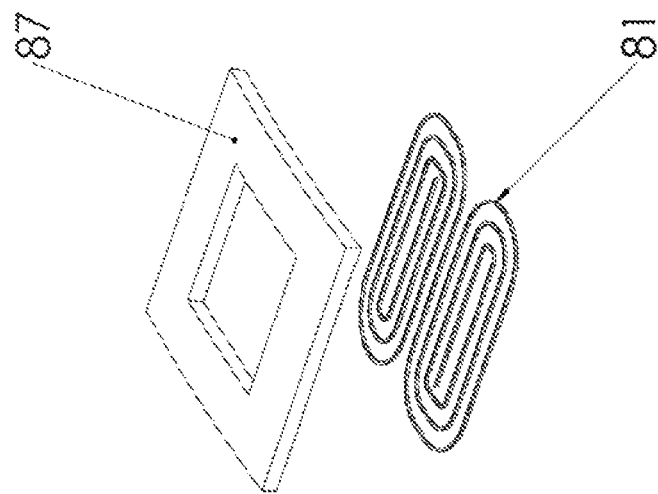
FIG. 8 is a perspective view of an EMAT coil and mask according to an embodiment of the present invention.

Also referring to FIG. 8, according to the exemplary configuration, NBSH transmitter-receiver coil 81 is in the form of a double-racetrack forming parallel wire segments or in an equivalent arrangement that includes a set of parallel wires carrying currents in the same direction. A coil shield 87 having a rectangular aperture, positioned to cover the outer wire segments and to leave exposed the central wires segments carrying current through the parallel wire segments in a same direction to thereby generate the normal beam shear horizontal waves.

In order to consolidate electronics and reduce the size of the tool, according to the exemplary configuration, the NBSH inspection transducer coil arrangement uses the same coil, e.g. in a double-racetrack form or equivalent form with parallel wires carrying currents in the same direction, as transmitter and receiver coil 81, whereas the SW and SV inspection transducer coil arrangement uses a different coil 83, e.g. in a meandering or equivalent form to create a set of parallel wires carrying currents in alternating directions, as transmitter coil and a plurality of smaller coils 85, either in the same form or in a different form, as receiver coils so as to have a one-to-many relationship between transmitter and receiver, and achieve a superior spatial mapping resolution of the defects. The SW and SV transducers, however, share the same transmitter-receiver coil combination.

Figure 9:
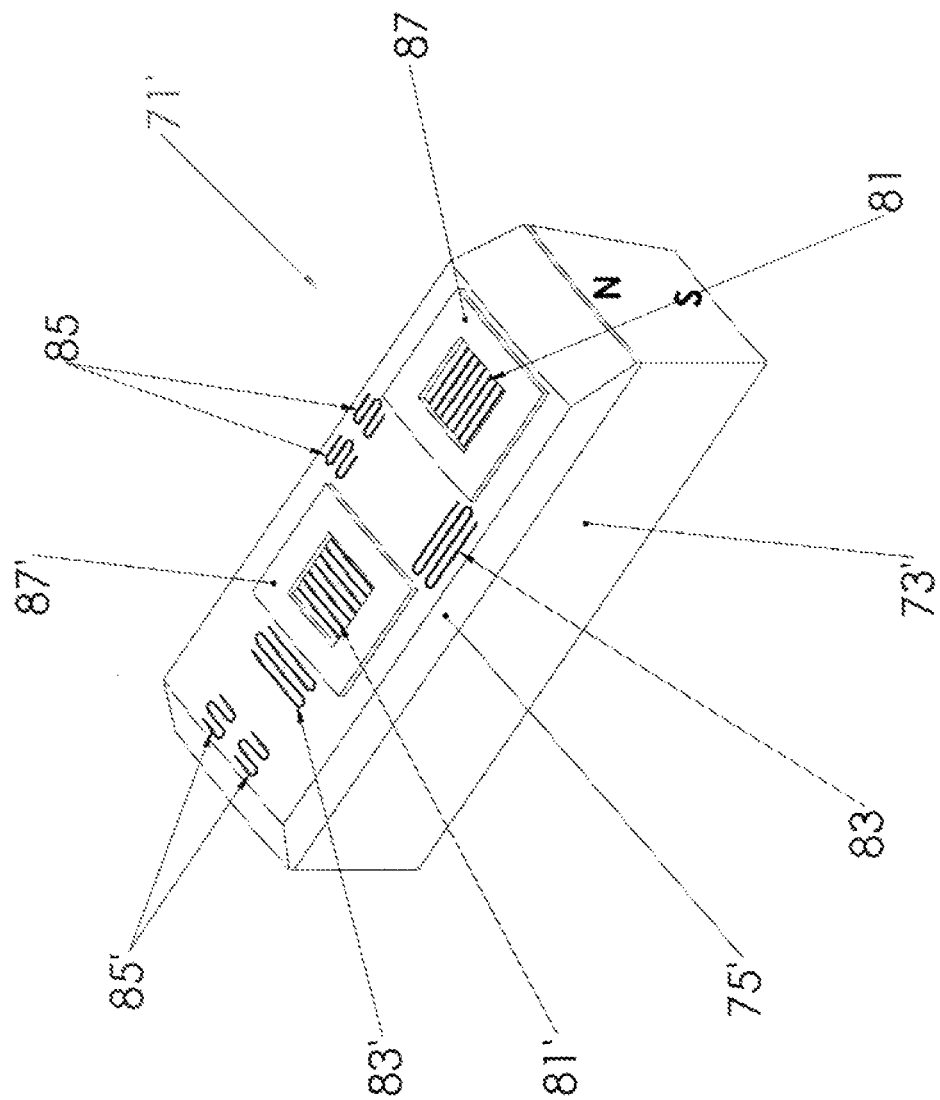
FIG. 9 is a perspective view of section module according to an embodiment of the present invention.

As shown in FIG. 9, according to an exemplary configuration, each module 71' includes a second NBSH transmitter-receiver coil 81' masked by a coil shield 87', a second surface wave-shear vertical transmitter coil 83', and a second plurality of surface wave-shear vertical receiver coils 85' each oriented substantially perpendicular with the longitudinal axis of the spine of the in-line tubular inspection device. The second NBSH transmitter-receiver coil 81' is arranged to propagate shear horizontal wave signals polarized in a direction orthogonal to the polarization direction of corresponding shear horizontal wave signals by the first NBSH transmitter-receiver coil 81 to thereby enhance the probability of defect detection in multiple different directions. Similarly, the second surface wave-shear vertical transmitter coil 83' is arranged to propagate surface wave signals in a direction orthogonal to a corresponding signals propagated by the first surface wave-shear vertical transmitter coil 83 and to propagate shear vertical wave signals in a direction orthogonal to the propagation direction of corresponding signals generated by the first surface wave-shear vertical transmitter coil to thereby enhance the probability of defect detection in multiple different directions.

Referring again to FIGS. 2 and 3, in an exemplary configuration, a plurality of identical modules 71 are arranged in a staggered manner into each of multiple telescoping sections 43 of the tool 31. FIG. 2 illustrates an example of such arrangement where two rows of modules 71, each containing four modules and both spanning along the circumference of the tool. Adjacent modules 71 within the rows of modules 71 are located next to each other in the axial direction and staggered circumferentially at a preselected increments such that one end of each row extends circumferentially beyond the other row by, e.g., one and a half modules.

When all telescoping sections 43 are assembled onto the spine 41 and fully collapsed, the extended ends of the rows of modules 71 will overlap circumferentially with the extended ends of the neighboring wedges without mechanical interference. When one or more or all of the telescoping sections 43 fully expand due to an increase in the inner diameter of the pipe or other tubular being inspected, the overlap between extended ends of neighboring sections 43 will reduce to a smaller extent but will not generate an excessive circumferential gap between them, ensuring a full (100%) coverage over the circumference of the pipe. In an exemplary configuration, the spacing of the modules 71 and alignment of the sections 43 allow for up to approximately a ±10% of variation in the ID of the pipe from its nominal size. Note, larger variations can be allowed but will generally require the use of additional module extensions.

According to the exemplary described configurations, the transmitter and receiver coils 81, 83, 85 (FIG. 7) and transmitter and receiver coils 81, 81', 83, 83', 85, 85' (FIG. 9) for each module 71 are located in the magnetic field produced by the same module magnet 73 and are maintained near the pipe inner surface. Two or more guides, e.g. wheels 91, are mounted on the free axial ends 93 of the telescoping section 43 to allow the respective section 43 to translate along and in contact with the internal surface of the pipe with a controlled liftoff of the pipe surface such that the electric coils are not too close to the pipe surface to cause damage to the coils nor too far from it to result in substantial signal degradation, allowing for the desired inspection performance.

The driver circuits (not shown) for the transmitter coils 81, 81', 83, 83', can be implemented in many ways, including using full H-bridge arrangements with high power Metal-Oxide-Semiconductor Field-Effect Transistor (MOSFETs) placed close to the transmitter coils to minimize voltage drop along the cables delivering the high current pulses to the transmitter coils.

The signal outputs of the receiver coils are typically very small. Accordingly, according to the exemplary configuration, a preamplifier is provided to mitigate potential electromagnetic noise and interference along the signal path prior to final amplification and processing occurring in the backend in the spine 41. The role of the preamplifier, is thus, to provide adequate signal gain while introducing as little input-referred noise as possible.

Referring to FIG. 3, an optional odometer system can be included into the tool head to measure the axial position of the tool inside the pipe. According to an exemplary embodiment, the odometer system includes one or more friction wheels 95 that have an elastomer tire bonded onto a metallic hub and one or more rotary encoders connected to the wheel axle for converting rotation into linear distance.

Referring to FIG. 1, the external subsystems 33 can include a position subsystem functioning as a primary if the tool head does not include an odometer subsystem, and can be optional as a backup if it does. The position subsystem can measure the axial position of the tool inside a pipe. The external subsystems 33 can also include a drive subsystem that moves the tool at a controlled speed using an electrical motor, for example. The external subsystems 33 can also include a power supply to provide power to the tool 31 and a user interface that runs on a personal computer, which can display the inspection results on a screen and receive user commands, e.g., to alter the threshold settings or control the drive subsystem.

The EMAT tubular inspection system 30 and in line tubular inspection device or tool 31 synergistically leverages the advantages of EMAT with innovative, tightly packaged high performance EMAT configurations to provide surprising results. Specifically, it utilizes different ultrasonic wave modes in a synergistic matter to measure wall thickness and detect pipe flaws with different spatial topology and orientations. The respective wave modes are generated with various combinations of magnetic field direction and electrical coil configuration.

According to the exemplary configuration, each module 71 of the tool 31 is capable of producing at least three wave modes, namely the Normal Beam Shear Horizontal (NBSH), Surface Wave (SW) and Shear Vertical (SV). These wave generating mode configurations are beneficially packaged into a single inspection tool 31 in a staggered manner, as described above, to achieve full 100 percent coverage of the ID and OD surfaces and the volume in between, over the entire length of the tubular portion of the pipe being inspected even when the ID of the pipe changes slightly due to deformation or buildup.

Among the three wave modes, as described above, the SW and SV wave modes may share the same magnetic field and coil configuration with the only differences being the driving frequencies of the excitation current flowing through the transmitter coil 83, 83', and the signal processing used to extract information from the respective modes. This design saves space and enables high performance of the tool within a compact tool size.

The NBSH wave propagates perpendicularly to the pipe surface and has a polarization direction parallel to the pipe surface. Due to the relatively small size of the transmitter-receiver coil 81, 81', compared to the diameter of the riser joint, the curvature of the pipe surface is anticipated to have only a minor effect on wave generation. As noted above, according to the exemplary configuration, the transmitter-receiver coil 81, 81' is a double-racetrack coil that has its outer portion of the wires masked by a thin conductor sheet 87 with a rectangular aperture at the center leaving only the central straight wires carrying the current in the same direction exposed to the pipe surface. This configuration of the transmitter-receiver coil 81, 81', in combination with the normal orientation of the magnetic field provided by the magnet 73, generates normal beam shear horizontal waves that can be employed to measure wall thickness and detect delamination flaws using pulse-echo time-of-flight method. The NBSH mode can also be used to detect far wall corrosion, far wall cracks in the main body or welds of the riser joint.

The SW wave propagates along the surface layer of the pipe and has a penetration depth of about a wavelength into the pipe wall, which is typically between approximately 1 mm to 10 mm, but can be larger in certain circumstances. The SW waves are most sensitive to, and thus, can be used to detect near wall surface breaking defects, e.g., near wall corrosions, cracks in the main body or welds, both axial and longitudinal, of the riser joint.

The SV wave propagates in an angled beam with respect to the surface normal, and has a polarization direction perpendicular to the propagation direction and within a plane formed by the surface normal and the propagation direction. The SV waves can be employed to detect cracks in the main body or welds of the riser joint. Transmitter coil 83 provides an example of the SW/SV modes employed using a meandering coil with conductor wires parallel to the device axis that generates circumferentially propagating surface waves or angle beam shear vertical waves.

Figure 10:
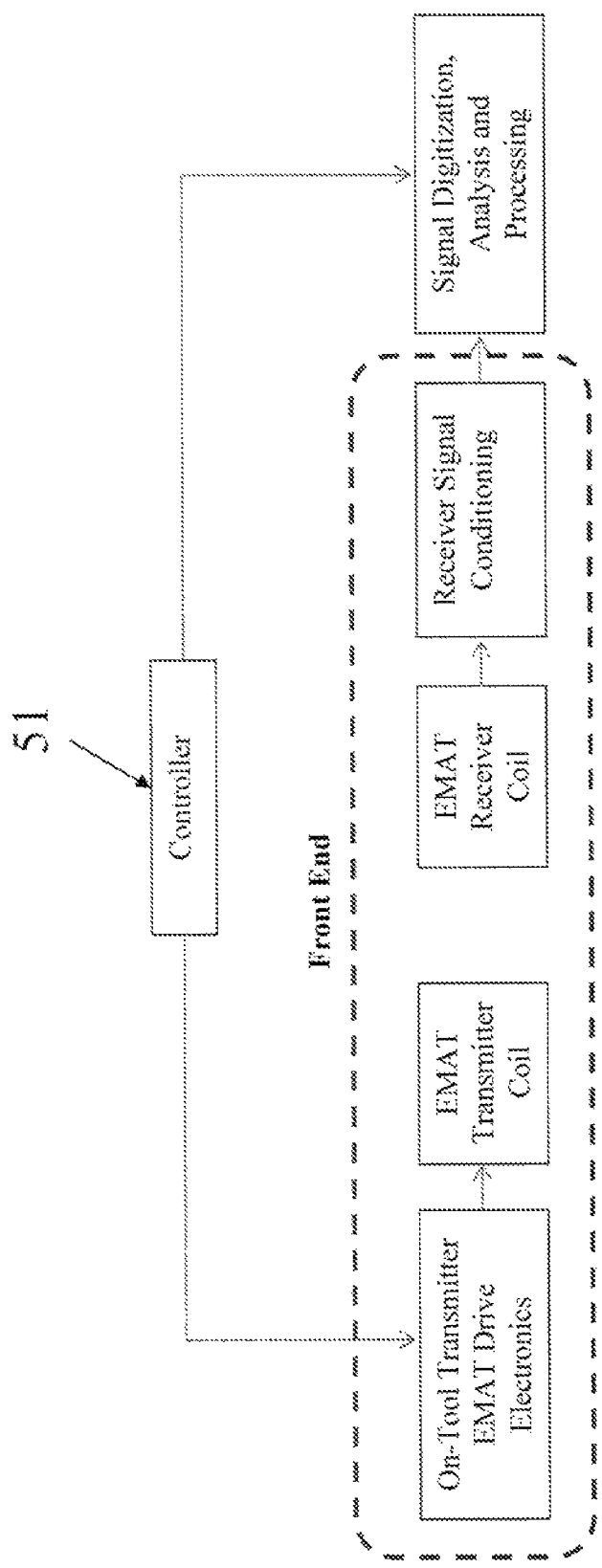
FIG. 10 is a block diagram of a signal chain according to an embodiment of the present invention.

FIG. 10 illustrates a block diagram of the signal chain for a signal channel for a single transmitter-receiver combination.

Figure 11:
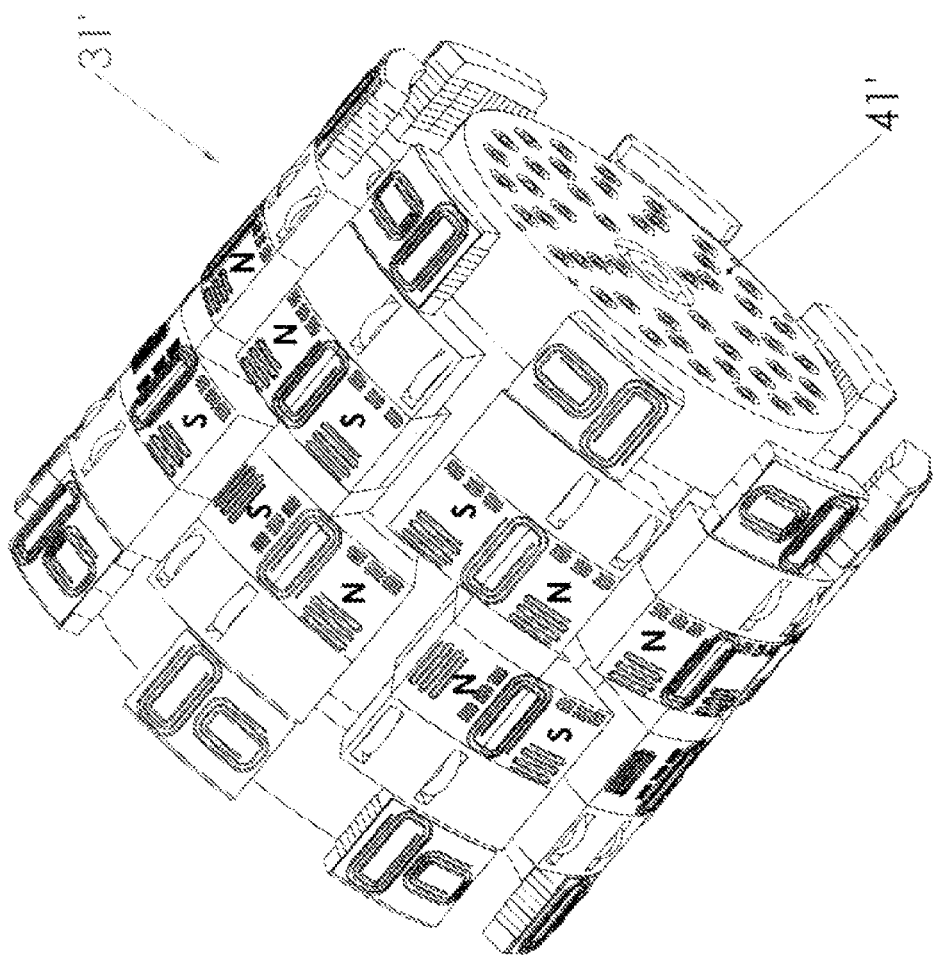
FIG. 11 is a perspective view of the side of an in-line tubular inspection device according to an embodiment of the present invention.

FIG. 11 illustrates in-line pipe inspection device 31' for an EMAT tubular inspection system according to another aspect of the invention. The inspection device 31' includes a set of two or more universal EMAT transducers configured such that when fired with electrical pulses, can be used to provide pipe wall measurements and the detection of pipe flaws in any spatial orientation, including but not limited to transverse cracks, longitudinal cracks, general corrosions, lamination flaws parallel to the surface of the pipe, and flaws in combined orientations, with radial flexibility allowing for variations of the inside diameter of the pipe while maintaining full 100 percent coverage of the pipe body along the scanned pipe length. The device 31' also includes an electronics assembly (not shown) to which the transducers are connected for controlling the frequency and the firing of the electrical components of the transducers (exciting coils) and for conditioning and amplifying the signals received from the pick-up coils of the transducers as a response to pipe flaws and obstacles such as wall boundaries. The device 31' can further include an odometer mechanism including one or two encoder-wheel pairs for measuring length and locating flaws along the axis of the pipe. The device 31' can additionally include a tangible computer readable medium that is readable by a computer, comprising a set of instructions that, when executed by a computer, causes the computer to send control commands to the electronics assembly of the device and receive inspection data from it and distance measurements from the odometer mechanism, and reporting the detection of pipe flaws and their location to the device operator.

Figure 12:
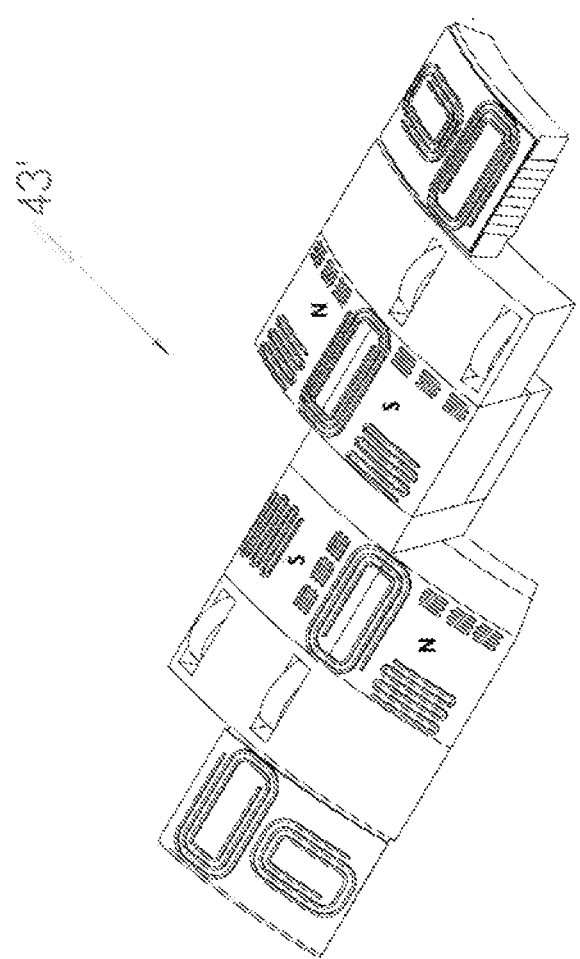
FIG. 12 is a perspective view of the top of a telescoping section of the in-line tubular spec sheet device of FIG. 11 according to an embodiment of the present invention.

FIG. 12 illustrates a telescoping section 43' shaped as a wedge with a triangular cross-section designed to be positioned perpendicular to the inner surface of a pipe being inspected. The section 43' is mounted on a spine 41' formed of a non-ferromagnetic material along radially oriented rails also formed of a non-ferromagnetic material. The telescoping section 43' is configured so that two or more transducers can be mounted around the spine 41' to form a flexible axially wedged cylinder of transducers capable of traversing a pipe with an internal diameter greater or equal to the diameter of the cylinder created by the transducers in their fully collapsed configuration and supporting irregular inside pipe diameters. FIG. 13 illustrates the device 31' with each of the telescoping sections 43' in an expanded position. FIG. 14 illustrates the device 31' with each of the telescoping sections 43' in a collapsed position.

Each telescoping section 43' can also include two or more wheels allowing it to roll on the internal surface of the pipe while maintaining a constant lift-off between the electrical coils of the transducer and the internal surface of the pipe.

Referring also to FIG. 15, each telescoping section 43' can include one or more pairs of magnets, permanent or pulsed, stacked at the center of the shear horizontal transducer coil along the axis of the pipe optionally separated by a spacer made out of a non-ferromagnetic material such that the outer surface of the magnet pairs is almost concentric and close to the inside surface of the pipe being inspected, and staggered circumferentially so that the plurality of telescoping sections 43' collectively provide full coverage of the internal pipe surface. Full coverage is ensured despite variations of the relative radial position of adjacent transducers due to the radial flexibility of the telescoping sections 43' which allows for supporting irregular inside pipe diameters.

According to the illustrated embodiment, the alternating magnets form a two dimensional matrix of two or more alternating magnets stacked along the axis of the pipe (also the axis of the inspection device) and along the circumferential direction of the pipe (also the circumferential direction of the inspection device) and mounted to the free side representing the axial end of each of the two wheel blocks of the telescoping section 43'. The polarity of each magnet in the matrix is radial with respect to the diameter of the pipe and opposite to the polarity of any adjacent magnet. The magnet arrangement also includes a mounting plate made out of a material non-conductive to electricity and mounted on top of each of the two blocks of alternating magnets such that the outer surface of the mounting plate is almost concentric and close to the inside surface of the pipe being inspected. Electrical coils of several possible configurations, including but not limited to racetrack coils, mounted on the two mounting plates of the telescoping section 43' such that they are positioned between the surface of the mounting plates and the surface of the pipe during inspection, which include two or more such blocks of alternating magnets being mounted next to each other circumferentially with different axial/longitudinal and circumferential/transverse orientations, enabling the generation of additional wave modes and enhancing the defect detection performance of the transducer.

Referring again to FIG. 12, the two magnets in each pair of magnets are mounted on one common ferromagnetic back iron and magnetized radially with opposite magnetic polarity so that the magnetic field is perpendicular to the surface of the pipe closest to the surface of the telescoping section 43' and so that any two axially adjacent magnets within the same section 43' and any two circumferentially adjacent magnets across adjacent sections 43' have the same magnetic polarity.

Each telescoping section 43' also includes electrical coils of several possible configurations, including but not limited to transverse and longitudinal meander coils, mounted on the outer surface of each magnet such that they are positioned between the magnet surface and the internal surface of the pipe being inspected. The electrical coils of several possible configurations, including but not limited to a longitudinal racetrack coil mounted on the outer surface of each magnet pair and positioned between the magnet surface and the internal surface of the pipe being inspected such that one half of the coil rests on one magnet and the other on the second magnet and the axial separation of the two magnets runs longitudinally through the center of the racetrack coil. The resulting magnetic circuit generates a normal magnetic field in the pipe section opposite to the magnets, and when combined with an electrical current running in the various configurations of the electrical coils, generates different desired wave modes inside the wall of the pipe allowing for pipe wall measurements and the detection of pipe flaws and defects. In this configuration, the wheels roll against the internal surface of the pipe with a controlled lift off of the pipe surface such that the electric coils are not too close to the pipe surface to cause damage to the coils nor too far from it, thus allowing for the desired inspection performance.

According to another exemplary configuration, mounted atop the magnet arrangement are a set of transverse meander coils with conductors running circumferentially and generating axially propagating vertically polarized bulk shear waves (angle beam) for the detection of transverse cracks, are staggered circumferentially. A racetrack coil mounted atop the center of the alternating magnets generates normal beam horizontally polarized shear waves for wall thickness measurement and detection of general corrosions and lamination flaws. A transverse racetrack coil generates circumferentially propagating horizontally polarized shear waves (angle beam) for the detection of longitudinal cracks. A longitudinal racetrack coil generates axially propagating horizontally polarized shear waves (angle beam) for the detection of transverse cracks. The coils are staggered circumferentially, further allowing for the detection of volumetric flaws (e.g., corrosion, pits) and planar pipe flaws along three reference orientations (in the three-dimensional space, transverse, longitudinal and tangent to the surface of the pipe), and enabling the detection of oblique flaws at non-zero angles from the reference orientations.

According to an exemplary embodiment, the firing of the various electrical coils follows specific controlling patterns to serialize and alternate firing of the electrical coils, to better manage power demand and eliminate interference between the various wave modes created by the multitude of electrical coils.

Another embodiment of the invention includes a method for inspecting the entire body of a pipe. The method can include the steps of sending high power pulses to the electrical coils of Universal Electro-Magnetic Acoustic Transducers (EMAT) transducers comprising several magnetic configurations and a variety of electrical coil configurations, and generating multiple wave modes for the detection of transverse, longitudinal and tangent pipe flaws; following specific controlling patterns to serialize and alternate firing of the electrical coils to better manage power demand and eliminate interference between the various wave modes created by the multitude of electrical coils. The method can also include the steps of receiving inspection data or signals from the EMAT transducers and distance measurements from an odometer mechanism, and reporting any pipe flaws detected by the EMAT transducers and their circumferential and axial location in the pipe to the operator.

Still another embodiment of the invention can include a system for inspecting the entire body of a pipe externally. The system can include an external pipe inspection device that wraps around the pipe like a clamshell. The embodiment of the external pipe inspection device can include a set of two or more External, Universal Electro-Magnetic Acoustic Transducers (EU-EMAT) configured such that when fired with electrical pulses they are capable of pipe wall measurements and the detection of pipe flaws in any spatial orientation, including but not limited to transverse cracks, longitudinal cracks, general corrosions, lamination flaws parallel to the surface of the pipe, and flaws in combined orientations, with radial flexibility allowing for variations of the outside diameter of the pipe while maintaining full (100%) coverage of the pipe body along the scanned pipe length. The system can include an electronics assembly to which all the EU-EMAT transducers are connected for controlling the frequency and the firing of the electrical components of the EU-EMAT transducers (exciting coils) and for conditioning and amplifying the signals received from the pick-up coils of the EU-EMAT transducers as a response to pipe flaws and obstacles such as wall boundaries. The system can also include an odometer mechanism including one or two encoder-wheel pairs for measuring length and locating flaws along the axis of the pipe, and a tangible computer readable medium including a set of instructions that when executed by a computer, cause the computer to send control commands to the electronics assembly of the device and receive inspection data from it and distance measurements from the odometer mechanism, and to report the detection of pipe flaws and their location to the device operator.

According to an exemplary configuration, each EU-EMAT Transducer is shaped as a wedge with a triangular cross-section perpendicular to the surface of the pipe being inspected allowing for mounting the EU-EMAT transducers on two halves of a clamshell structure made out of non-ferromagnetic material and allowing for the EU-EMAT transducers to slide in closer to the pipe and out away from the pipe along radially oriented rails also made out of non-ferromagnetic material so that two or more EU-EMAT transducers can be mounted on each half of the clamshell structure. Each EU-EMAT Transducer further includes two or more wheels allowing it to roll on the external surface of the pipe while maintaining a constant lift-off between the electrical coils of the EU-EMAT transducer and the external surface of the pipe.

Each EU-EMAT Transducer can include two or more magnet pairs, two or more wheel mounting blocks, two or more blocks of alternating magnets and the associated electrical coils described previously with respect to the prior embodiments, but with a concave shape circumferentially concentric to the pipe allowing the wedge surface to be parallel to the external pipe surface.

According to this embodiment, the firing of the various electrical coils on the EU-EMAT Transducers follows specific controlling patterns to serialize and alternate firing of the electrical coils, better manage power demand and eliminate interference between the various wave modes created by the multitude of electrical coils.

Another embodiment of the invention includes a method for inspecting the entire body of a pipe externally. The method can include the steps of sending high power pulses to the electrical coils of External Universal Electro-Magnetic Acoustic Transducers (EU-EMAT) including several magnetic configurations and a variety of electrical coil configurations and generating multiple wave modes for the detection of transverse, longitudinal and tangent pipe flaws. The steps can also include following specific controlling patterns to serialize and alternate firing of the electrical coils to better manage power demand and eliminate interference between the various wave modes created by the multitude of electrical coils, receiving inspection data or signals from the EU-EMAT transducers and distance measurements from an odometer mechanism, and reporting any pipe flaws detected by the EU-EMAT transducers and their circumferential and axial location in the pipe to the operator.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

That invention claimed is:

1. An electro-magnetic acoustic transducers (EMAT) in-line tubular inspection device comprising:
    a spine comprising a longitudinal support body and a plurality radially projecting rails extending therefrom; and
    a plurality of telescoping sections each connected to at least two of the plurality of radially projecting rails, each of the plurality of telescoping sections comprising:
        a back panel,
        one or more guide mounts each including one or more surface engagement mechanisms positioned to engage an inner surface of a body of a tubular during inspection thereof, and
        a plurality of signal propagating and receiving modules carried by the back panel, each module comprising a magnet operably connected to the back panel and a plurality of different types of EMAT inspection transducer coil arrangements operably connected to an outer surface portion of the magnet, the plurality of different types of EMAT inspection transducer coil arrangements providing for the generation of NBSH, SW, and SV waves.

2. An EMAT in-line tubular inspection device as defined in claim 1,
    wherein the back panel is a magnetic back panel;
    wherein the plurality of different types of EMAT inspection transducer coil arrangements are a first plurality of different types of EMAT inspection transducer coil arrangements connected to a first outer surface portion of the magnet and including respective transducer transmitting and receiving coils oriented substantially parallel with a longitudinal axis of the longitudinal support body of the spine of the in-line tubular inspection device; and
    wherein each module of the plurality of signal propagating and receiving modules further comprise a second plurality of the different types of EMAT inspection transducer coil arrangements connected to a second outer surface portion of the magnet to provide for the generation of NBSH, SW, and SV waves, and including respective transducer transmitting and receiving coils oriented substantially perpendicular to the longitudinal axis of the longitudinal support body of the spine.

3. An EMAT in-line tubular inspection device as defined in claim 2,
    wherein a first plurality of different types of EMAT inspection transducer coil arrangements comprises a first NBSH transmitter-receiver coil, a first surface wave-shear vertical transmitter coil, and a first plurality of surface wave-shear vertical receiver coils each oriented substantially parallel with the longitudinal axis of the spine of the in-line tubular inspection device;
    wherein a second plurality of different types of EMAT inspection transducer coil arrangements comprises a second NBSH transmitter-receiver coil, a second surface wave-shear vertical transmitter coil, and a second plurality of surface wave-shear vertical receiver coils each oriented substantially perpendicular with the longitudinal axis of the spine of the in-line tubular inspection device;
    wherein the second NBSH transmitter-receiver coil is arranged to propagate shear horizontal wave signals polarized in a direction orthogonal to the polarization direction of corresponding shear horizontal wave signals by the first NBSH transmitter-receiver coil to thereby enhance defect detection in multiple directions, both the shear horizontal waves propagated by the first NBSH transmitter-receiver coil and by the second NBSH transmitter-receiver coil being propagated in a direction normal to the inner surface of the body of the tubular adjacent to the respective first and second NBSH transmitter-receiver coil; and
    wherein the second surface wave-shear vertical transmitter coil is arranged to propagate surface wave signals in a direction along the inner surface of the body of the tubular adjacent to the surface wave-shear vertical transmitter coil and orthogonal to the propagation direction of the surface wave signals generated by the first surface wave-shear vertical propagation transmitter coil and to propagate shear vertical wave signals in a direction orthogonal to the propagation direction of corresponding signals generated by the first surface wave-shear vertical transmitter coil to thereby enhance defect detection in multiple directions.

4. An EMAT in-line tubular inspection device as defined in claim 1, wherein each of the plurality of telescoping sections comprises:
   a plurality of the guide mounts; and
   a plurality of wedge-shaped subsections each having a radial cross-section described by a pair of converged lateral sides, a concave inner surface, and a convex outer surface and sharing the magnetic back panel for the respective telescoping section, each of the plurality of wedge-shaped subsections comprising a separate one of the plurality of guide mounts.

5. An EMAT in-line tubular inspection device as defined in claim 1, wherein the plurality of telescoping section are staggered in an overlapping manner to achieve full 100 percent coverage of ID and OD surfaces and volume therebetween over a entire length of the body of the tubular during inspection thereof, the body of the tubular being characterized by having inner diameter that varies due to deformation in one or more portions of the body of the tubular or buildup of non-tubular material.

6. An EMAT in-line tubular inspection device as defined in claim 1, wherein the plurality of telescoping section are staggered in an overlapping manner to ensure full 100 percent coverage over the inner surface of the body of the tubular during inspection thereof, with up to approximately ±10 percent of variation in ID from the nominal size thereof.

7. An EMAT in-line tubular inspection device as defined in claim 6, wherein the plurality of telescoping sections slidably engage the at least two of the plurality of rails to expand due to an increase in inner diameter of the body of the tubular during inspection thereof and to thereafter retract due to a decrease in inner diameter, an overlap between extended ends of neighboring sections being sufficient so that a corresponding reduction in the overlap resulting from expansion resulting from the increase in inner diameter of the body does not generate a circumferential gap between the plurality of telescoping sections sufficient to reduce coverage below 100 percent when the variation in the inner diameter from the nominal size thereof is less than the approximately ±10 percent.

8. An EMAT in-line tubular inspection device as defined in claim 1, wherein the plurality of different types of EMAT inspection transducer coil arrangements for each of multiple of the plurality of signal propagating and receiving modules for each of multiple of the plurality of telescoping sections include a surface wave-shear vertical transducer coil arrangement consolidating transmitting and receiving functions for an associated combination of surface and shear waves into a respective common transmitting coil using a different set of driving frequencies and excitation currents applied thereto to produce the respective surface wave and shear wave having vertical polarization, and a respective common set of one or more receiver coils, with each of the common transmitting and receiving coils positioned within a common magnetic field, to thereby reduce total size of the inspection device.

9. An EMAT in-line tubular inspection device as defined in claim 1, wherein the spine further carries an electronics assembly including electronics components configured to provide for detection of volumetric flaws, planar flaws along three reference orientations, and oblique flaws at non-zero angles from the three reference orientations, in the body of the tubular, the electronics components including a system controller, a received signal digitizer, and a received signal processing unit.

10. An electro-magnetic acoustic transducers (EMAT) tubular inspection system for inspecting a body of a tubular comprising the in-line tubular inspection device as defined in claim 1, wherein the longitudinal support body of the spine of the inter-line tubular inspection device comprises:
   a plurality of apertures housing a plurality of electronic components configured to provide for detection of volumetric flaws, planar flaws along three reference orientations, and oblique flaws at non-zero angles from the three reference orientations; and
   a central passageway extending at least partially therethrough for receiving an umbilical cable configured to interface with one or more of the electronic components of the electronics assembly.

11. An electro-magnetic acoustic transducers (EMAT) in-line tubular inspection device comprising:
   a spine comprising a longitudinal support body, a plurality radially projecting rails, a passageway extending therethrough to receive an umbilical cable, and an electronics assembly configured to control transmission frequency and firing sequence of each of a plurality of signal propagating EMAT inspection transducers and to condition and amplify signals received from a plurality of signal receiving EMAT inspection transducers to thereby determine far wall corrosion, near wall corrosion, pitting, transverse cracks in the body of the tubular, longitudinal cracks in the body of the tubular, transverse weld defects, longitudinal weld defects, and delamination, when existing, and wall thickness measurement, the electronics assembly comprising a system controller, a received signal digitizer, and a received signal processing unit; and
   a plurality of telescoping sections each slidably connected to at least two of the plurality of radially projecting rails and staggered in an overlapping manner to achieve full 100 percent coverage of ID and OD surfaces and volume therebetween over a entire length of the body of the tubular during inspection thereof, the body of the tubular being characterized by having inner diameter that varies due to deformation or buildup, each of the plurality of telescoping sections comprising:
      a magnetic back panel,
      one or more guide mounts each including one or more surface engagement mechanisms positioned to engage an inner surface of the body of a tubular, and
      a plurality of signal propagating and receiving modules carried by the magnetic back panel, each module comprising:
         a magnet operably connected to the magnetic back panel,
         a signal generator,
         a received signal amplifier,
         a first plurality of different types of EMAT inspection transducer coil arrangements operably connected to a first outer surface portion of the magnet to provide for the generation of NBSH, SW, and SV waves, and including respective transducer transmitting and receiving coils oriented substantially parallel with a longitudinal axis of the longitudinal support body of spine, and
         a second plurality of the different types of EMAT inspection transducer coil arrangements connected to a second outer surface portion of the magnet to provide for the generation of NBSH, SW, and SV waves, and including respective transducer transmitting and receiving coils oriented substantially perpendicular to the longitudinal axis of the longitudinal support body of the spine.

12. An EMAT in-line tubular inspection device as defined in claim 11,
wherein a first plurality of different types of EMAT inspection transducer coil arrangements comprises a first NBSH transmitter-receiver coil, a first surface wave-shear vertical transmitter coil, and a first plurality of surface wave-shear vertical receiver coils each oriented substantially parallel with the longitudinal axis of the spine of the in-line tubular inspection device;
wherein a second plurality of different types of EMAT inspection transducer coil arrangements comprises a second NBSH transmitter-receiver coil, a second surface wave-shear vertical transmitter coil, and a second plurality of surface wave-shear vertical receiver coils each oriented substantially perpendicular with the longitudinal axis of the spine of the in-line tubular inspection device;
wherein the second NBSH transmitter-receiver coil is arranged to propagate shear horizontal wave signals polarized in a direction orthogonal to the polarization direction of corresponding shear horizontal wave signals by the first NBSH transmitter-receiver coil to thereby enhance defect detection in multiple directions, both the shear horizontal waves propagated by the first NBSH transmitter-receiver coil and by the second NBSH transmitter-receiver coil being propagated in a direction normal to the inner surface of the body of the tubular adjacent to the respective first and second NBSH transmitter-receiver coil; and
wherein the second surface wave-shear vertical transmitter coil is arranged to propagate surface wave signals in a direction along the inner surface of the body of the tubular adjacent to the surface wave-shear vertical transmitter coil and orthogonal to of the propagation direction of the surface wave signals generated by the first surface wave-shear vertical transmitter coil and to propagate shear vertical wave signals in a direction orthogonal to the propagation direction of corresponding signals generated by the first surface wave-shear vertical transmitter coil to thereby enhance defect detection in multiple directions.

13. An EMAT in-line tubular inspection device as defined in claim 11, wherein each of the plurality of telescoping sections comprises:
a plurality of the guide mounts; and
a plurality of wedge-shaped subsections each having a radial cross-section described by a pair of converged lateral sides, a concave inner surface, and a convex outer surface and sharing the magnetic back panel for the respective telescoping section, each of the plurality of wedge-shaped subsections comprising a separate one of the plurality of guide mounts.

14. An EMAT in-line tubular inspection device as defined in claim 11, wherein the plurality of telescoping sections slidably engage the at least two of the plurality of rails to expand due to an increase in inner diameter of the body of the tubular during inspection thereof and to thereafter retract due to a decrease in inner diameter, an overlap between extended ends of neighboring sections being sufficient so that a corresponding reduction in the overlap resulting from expansion resulting from the increase in inner diameter of the body does not generate a circumferential gap between the plurality of telescoping sections sufficient to reduce coverage below 100 percent when the variation in the inner diameter from the nominal size thereof is less than ±10 percent.

15. An EMAT in-line tubular inspection device as defined in claim 11, wherein the plurality of magnets of each of the plurality of signal propagating and receiving modules comprises a plurality of radially magnetized magnets collectively having sufficient strength to maintain the one or more surface engagement mechanisms of the one or more guide mounts of the respective telescoping section in contact with the inner surface of the body of the tubular during operational inspection thereof, the tubular having an inner diameter that varies due to deformation or buildup.

16. An EMAT in-line tubular inspection device as defined in claim 15, wherein each magnet comprises a pole cap formed of ferromagnetic material configured to concentrate the magnetic field produced therefrom in a portion of the body of the tubular adjacent thereto during inspection thereof.

17. An EMAT in-line tubular inspection device as defined in claim 11,
wherein the first plurality of different types of EMAT inspection transducer coil arrangements for each of multiple of the plurality of signal propagating and receiving modules for each of multiple of the plurality of telescoping sections include a first surface wave-shear vertical transducer coil arrangement consolidating transmitting and receiving functions for an associated first combination of surface and shear waves into a respective first common transmitting coil using a different set of driving frequencies and excitation currents applied thereto to produce the respective surface wave and shear wave having vertical polarization, and a respective first common set of one or more receiver coils, with each of the respective common transmitting and receiving coils positioned within a common magnetic field, to thereby reduce total size of the inspection device; and
wherein the second plurality of different types of EMAT inspection transducer coil arrangements for each of the multiple of the plurality of signal propagating and receiving modules for each of the multiple of the plurality of telescoping sections include a second surface wave-shear vertical transducer coil arrangement consolidating transmitting and receiving functions for an associated second combination of surface and shear waves into a respective second common transmitting coil using a different set of driving frequencies and excitation currents applied thereto to produce the respective surface wave and shear wave having vertical polarization, and a respective second common set of one or more receiver coils, with each of the respective common transmitting and receiving coils positioned within the common magnetic field, to thereby reduce total size of the inspection device.

18. An EMAT in-line tubular inspection device as defined in claim 11, wherein the first plurality of different types of EMAT inspection transducer coil arrangements comprises a first NBSH transmitter-receiver coil, wherein the second plurality of different types of EMAT inspection transducer coil arrangements comprises a second NBSH transmitter-receiver coil, and wherein each of the first and the second NBSH transmitter-receiver coils comprise:
a double-racetrack coil forming parallel wire segments, and
a coil shield having a rectangular aperture, positioned to cover a plurality of outer wire segments and to leave exposed a plurality of central wires segments carrying current through the parallel wire segments in a same direction to thereby generate the normal beam shear horizontal waves.

19. A method of inspecting a body of a tubular, the method comprising the steps of:
   positioning an in-line tubular inspection device to establish a magnetic field between each of a plurality of telescoping sections of the device and respective portions of the body of the tubular adjacent thereto and to form a magnetic coupling with the respective adjacent portion of the body of the tubular;
   maintaining a preselected distance between a plurality of different types of EMAT inspection transducer coil arrangements of each of one or more signal propagating and receiving modules of each of the plurality of telescoping sections and inner surface portions of the body of the tubular adjacent thereto through employment of a respective one or more guide mounts and through the maintaining of the magnetic coupling with the respective adjacent portion of the body of the tubular;
   sending electrical signals having a preselected duration, frequency, and sequence to a transmitter coil of each of the plurality of different types of EMAT inspection transducer coil arrangements to thereby generate NBSH, SW, and SV waves;
   receiving signals produced as a result of the step of sending the electrical signals; and
   conditioning and amplifying the received signals to thereby identify a plurality of flaws in the body of the tubular, the plurality of flaws comprising volumetric flaws, planar flaws along three reference orientations, and oblique flaws at non-zero angles from the three reference orientations.

20. A method of inspecting a body of a tubular as defined in claim 19, wherein each of the plurality of telescoping sections slidably engage at least two of a plurality of radially projecting rails to expand due to an increase in inner diameter of the body of the tubular during inspection thereof and to thereafter retract due to a decrease in inner diameter, the step of maintaining a preselected distance comprising the steps of:
   automatically radially retracting one or more of the plurality of telescoping sections responsive to encountering an area of reduced inner diameter of the body of the tubular resulting from a deformation in the respective area of the body of the tubular or buildup of non-tubular material; and
   automatically radially extending the one or more of the plurality of telescoping sections responsive to passage of the area of increased inner diameter.

21. A method of inspecting a body of a tubular as defined in claim 19, wherein the plurality of telescoping sections are staggered in an overlapping manner to achieve full 100 percent coverage of ID and OD surfaces and volume therebetween over a entire length of the body of the tubular during inspection thereof within a substantial predetermined variation in ID from the nominal size thereof, the body of the tubular being characterized by having inner diameter that varies due to deformation in one or more portions of the body of the tubular or buildup of non-tubular material.

22. A method of inspecting a body of a tubular as defined in claim 21, wherein an overlap between extended ends of neighboring sections are sufficient so that a corresponding reduction in the overlap resulting from expansion resulting from the increase in inner diameter of the body does not generate a circumferential gap between the plurality of telescoping sections sufficient to reduce coverage below 100 percent when the variation in the inner diameter from the nominal size thereof is less than approximately ±10 percent.

23. A method of inspecting a body of a tubular as defined in claim 19, wherein a magnetic field generator of each of the one or more signal propagating and receiving modules of one or more of the plurality of telescoping sections is a corresponding radially magnetized magnet, and wherein the plurality of different types of EMAT inspection transducer coil arrangements comprise:
   a first plurality of different types of EMAT inspection transducer coil arrangements operably connected to a first outer surface portion of the magnet, the respective transmitting and receiving coils oriented substantially parallel with a longitudinal axis of a longitudinal support body of a spine of the in-line tubular inspection device, and
   a second plurality of the different types of EMAT inspection transducer coil arrangements connected to a second outer surface portion of the magnet, the respective transducer transmitting and receiving coils oriented substantially perpendicular to the longitudinal axis of the longitudinal support body of the spine.

24. A method of inspecting a body of a tubular as defined in claim 19, wherein the transmitter coil and one or more receiver coils for one of the plurality of different types of EMAT inspection transducers for the one or more signal propagating and receiving modules for each of multiple of the plurality of telescoping sections are comprised by a surface wave-shear vertical transducer coil arrangement consolidating transmitting and receiving functions for an associated combination of surface and shear waves into a respective common transmitting coil using a different set of driving frequencies and excitation currents applied thereto to produce the respective surface wave and shear wave having vertical polarization, and a respective common set of one or more receiver coils, with each of the common transmitting and receiving coils positioned within a common magnetic field produced by a magnetic field generator of the one or more signal propagating and receiving modules, to thereby reduce total size of the inspection device.

* * * * *